United States Patent [19]
Khaledi et al.

[11] Patent Number: 5,561,177
[45] Date of Patent: Oct. 1, 1996

[54] HYDROCARBON FREE DENTURE ADHESIVE

[75] Inventors: Nilofar Khaledi, Hackensack; Eddie Wong, New Providence; Joseph Synodis, Summit, all of N.J.; Hal C. Clarke, Elmont, N.Y.; Robert C. Gasman, Montville; Alfred J. Smetana, Wayne, both of N.J.

[73] Assignee: The Block Drug Company, Jersey City, N.J.

[21] Appl. No.: 495,282

[22] Filed: Jun. 27, 1995

[51] Int. Cl.[6] ............... C08L 1/00; C08L 1/26; C08L 91/00; A61K 6/00
[52] U.S. Cl. ............... 524/35; 524/43; 524/45; 524/313; 524/492; 523/120; 433/180
[58] Field of Search ............... 524/35, 43, 45, 524/313, 492; 523/120; 433/180

[56] References Cited

U.S. PATENT DOCUMENTS

| | | | |
|---|---|---|---|
| 4,569,955 | 2/1986 | Dhabhar | 523/120 |
| 5,093,387 | 3/1992 | Schobel et al. | 523/120 |
| 5,298,534 | 3/1994 | Prosise et al. | 523/120 |

*Primary Examiner*—Paul R. Michl
*Assistant Examiner*—LaVonda DeWitt
*Attorney, Agent, or Firm*—Craig M. Bell; Dann, Dorfman, Herrell and Skillman

[57] ABSTRACT

An improved denture adhesive that exhibits superior tack, adhesion, cohesive strength and spreadability characteristics is made from a hydrocarbon-free base consisting of a mixture of medium length chain triglycerides which have been mixed with a small amount of fumed silica and other components so as to improve the viscosity, spreadability and taste. Preferred triglycerides include captic and caprylic acids and in particular, a mixture of the caprylic and captic acids which are combines with fumed silica and a water soluble cellosic polymer and a synthetic methyl vinyl ether/ maleic anhydride copolymer that is formulated as a paste or gel.

20 Claims, No Drawings

HYDROCARBON FREE DENTURE ADHESIVE

FIELD OF THE INVENTION

The present invention relates generally to denture adhesives for affixing dental prosthesis to oral tissues of the jaw and upper mouth regions.

BACKGROUND OF THE INVENTION

Traditionally, adherent creams and powders used to secure dentures within the mouth were prepared from such materials as finely powdered natural gums, i.e. karaya, acacia or tragacanth gum. These materials have the particular property of swelling to many times their original volume upon the addition of water to form a gelatinous or mucilaginous mass. Denture adhesive powders may be a combination of one or more natural gums, generally flavored with pleasant tasting volatile oils. Many other additives may also be included such as antiseptics, stabilizers, bactericides, special deodorants, plasticizing agents, fillers, coloring agents, and the like.

Cream forms of denture adherents, prepared from finely ground particles of the natural gums dispersed in a cream base, are also available and may be used instead of powder compositions. In any event, when wet with water, the natural gum in either the cream or powder formulation expands to become a viscous gel which acts as a cushion and an adherent between the denture plate and the gum tissue.

Denture adhesive cream formulations have also been comprised mainly of natural or synthetic polymer materials suspended in an anhydrous oleaginous vehicle system comprising mineral oil and petrolatum. The petrolatum is added to thicken the formulation consistency to that of a cream which is extrudable from tubes. These formulations necessarily must be thick to prevent syneresis or phase separation because the solid adhesive particles are merely suspended in the oily vehicle. This thickness of the formulation makes them somewhat difficult to squeeze out from the tube.

Additionally, although these formulations are fairly thick in consistency at ambient room temperature of about 25° C., they are not thermally very stable and hence tend to thin out evenly at slightly elevated temperatures. For example, at the body/mouth temperature of 37° C. at which these formulations are used, they tend to thin out and become runny and therefore ooze out from under the denture during use. The phenomenon is naturally further aggravated when hot liquids and foods are consumed by denture wearers who use such denture adhesive products. This problem with oozing of denture adhesive from under the denture into the mouth is considered to be one of the major drawbacks to the consumer due to the unpleasant taste and mouth feel. Additionally, the holding property of the formulation that secures the prosthesis to the jaw is reduced due to the oozing or loss of product from under the denture.

One extremely desirable attribute of a good denture adhesive is that it develops a high degree of tack upon contact with saliva in order that the dentures be held in place as soon as they are seated in the mouth. It is also highly desirable that the mucilage is spread over the denture-mucosa interface in order to effectively seal the denture in place and that the mucilage possesses sufficient cohesive strength to withstand the stresses of mastication which act to rupture the seal and thus dislodge the denture. The denture fixation must also exhibit sufficient resistance to degradation under the extreme environmental temperature changes which occur in the oral cavity during such common actions as drinking coffee or other hot beverages and foods.

The dental adhesive compositions of the present invention afford the excellent adhesion of the dentures to the oral tissues of the gums and jaw regions of the mouth while at the same time are non-toxic so as to not adversely affect these same oral tissues. The adhesive cream provides excellent cohesive properties with a high degree of tack to prevent denture sliding. The composition possesses a soft, creamy texture with no unpleasant taste or mouthfeel.

Historically, a denture adhesive cream is made by preparing a base and mixing the base with other components which will provide sufficient adhesion with adequate cohesive strength to hold the dentures in place. This adhesive cream must be non-toxic and non-irritating to oral tissues since they are in direct contact with the tissues and the dental prostheses. For a denture adhesive to be practical and provide comfort, it must not have an unpleasant odor and must have a pleasant taste and aroma. It also must exhibit adequate stability, and quickly hydrate when in contact with the oral mucosa. It must also provide sufficient tack to form a strong cohesive strength and must be durable. In addition to all of the above, product appearance and the ease of application of the product are also significant factors.

The dental adhesive composition must not only hydrate when contacted with oral fluids in order to form both a cushion and a cohesive seal with the oral tissues of the maxillary arch or inner surface of the mandible, but it must also at the same time not be soluble when exposed to these same fluids such as saliva and the various foods and beverages that are exogenously introduced into the mouth.

Denture adhesive creams and powders are well known in the art and many commercially available products have been around for quite some time. The materials comprising these denture adhesives have varied but generally have remained somewhat constant in order to provide the necessary functional attributes. Oils, fatty acids esters, petrolatum and combinations of these have always been used as the primary components to produce the adhesive cream base. The use of hydrophilic colloids, active ingredients, flavors, dyes, sweeteners, therapeutic agents and preservatives in the vehicle in order to prepare a uniform paste have also been practiced in the development of a denture adhesive cream. All these require the presence of a hydrocarbon mineral oil to act as a solvent and thickener for the adhesive cream base.

U.S. Pat. No. 4,318,742 to Lokken discloses and claims a denture adhesive comprised of a major amount of gum base consisting of natural and synthetic gums, isobutylene/isoprene rubber, petrolatum waxes, polyethylene and mixtures thereof. The gum base is combined with a hydrophilic polymer such as methacrylic acid esters and carboxymethyl cellulose and the like to form the adhesive which may include other excipients such as plasticizers, tackifiers, sweeteners, flavors and the like to modify the adhesives sensory and theological characteristics.

U.S. Pat. No. 4,521,551 to Chang et al. teaches and claims various denture fixative compositions comprising a water soluble partially neutralized alkyl vinyl ether maleic acid/anhydride copolymer and at least one hydrophilic polymer such as sodium carboxymethyl cellulose polyethylene oxide or hydroxypropyl guar. When contacted with salvia said composition develops a high degree of tack and viscous mucilage which readily spreads over the denture-mucosal interface so as to fill the gaps between the dentures and gum and provides a suction-type seal.

U.S. Pat. No. 5,006,571 to Kumar et al. describes a denture adhesive composition consisting of petrolatum, natural and synthetic oils, waxes, vegetable oil waxes and the like. The useful oils mentioned include mineral oil, vegetable oils such as corn, soy bean, cottonseed, castor, palm and coconut oils and animal oil such as fish oil and oleic acid. In general, the oils are incorporated in amounts of about 1.0% to about 30.0% by weight of the total denture adhesive composition with amounts of from about 10% to about 25% being preferred. An optional component in the formulation of the invention is the use of fumed silica in the amount of about 0.5% to 6.0%..

U.S. Pat. No. 5,093,387 to Schobel et al. discloses a denture adhesive base composition with an anhydrous mixture of cationic derivatives of guar gum, a mixed sodium/calcium salt of methyl vinyl ether maleic anhydride and sodium carboxymethyl cellulose. Fumed silica is disclosed as an optional additive in the formulation of the adhesive. The cream base material also includes a selected group of natural and synthetic oils and mixtures thereof. At least one cream base material is selected from the group of petrolatum, synthetic oils and mixtures thereof. There is no teaching of a natural oil or vegetable oil with fumed silica as total replacement of the hydrocarbons in the vehicle.

None of the prior art has successfully formulated a dental cream adhesive base that is free of hydrocarbon mineral oils which impact a far lesser degree of objectionable odor and taste. The novel adhesive base composition of the present invention is thickened with fumed silica which imparts a low viscosity to the cream, a far better spreadability yet still maintains a high level of cohesion.

DETAILED DESCRIPTION OF THE INVENTION

The objective of the present invention is to develop a new and improved denture adhesive composition which is free of hydrocarbon mineral oils and is derived from vegetable sources that are non-toxic with quick hydration and excellent hold properties. The denture adhesive provides acceptable adhesion when in contact with the oral mueosa, and provide excellent cohesive strength while maintaining its hold properties for an extended period of time. Furthermore, this denture adhesive has a fast rate of hydration which makes it an ideal system when in contact with saliva.

This vegetable oil, comprised of caprylic/capric triglycerides is a triglyceride of medium chain fatty acids where the —C=O—R group is 8–10 carbons and is obtained by the addition of glycerol to a mixture of capric and caprylic acids:

Caprylic acid: $CH_3(CH_2)_6CO_2H$
Capric acid: $CH_3(CH_2)_8CO_2H$

This odorless, low viscosity (23 cps) vegetable oil is derived from eatable sources and its bland character makes it an ideal vehicle for flavors or medicaments. The acid value of this oil is limited to 0.1 and its hydroxyl value is also limited to 5 in order to ensure that all fatty acids are esterified to triglyeerides, since even small traces medium chain monoglycerides give a very bitter taste in the final oil. The medium chain triglycerides have a remarkably low iodine value with an upper limit of 0.5, and this amount of unsaturation is not significant in the oxidation stability of the oil. This oil has a peroxide value of 0.5 max. Samples of various oils have been heated up to 140° C. and their peroxide values have been periodically determined. The peroxide value of the high oleic acid sunflower oil (with peroxide value of 10) had been exceeded after 1.5 hours. Also, the partly hydrogenated soybean oil peroxide value was increased after 3 hours. The medium chain triglycerides, however showed a peroxide value of less than 2 even after 100 hours at this high temperature.

It has also been found that oils with a high content of unsaturated fatty acids polymerize under the influence of heat and oxygen. This can be seen by an increase in the viscosity of the product. Hybrid safflower oil is virtually odorless, but since it is an unsaturated fatty acid, it is easily oxidized. The hybrid safflower oil and fumed silica were studied at elevated temperature and the adhesive became rancid. The viscosity of the adhesive increased and the product was difficult to be extruded out of tubes.

In the present invention then, all of the hydrocarbon solvents and additives required by the denture adhesive compositions of the prior art have been replaced by vegetable oils comprised of saturated medium chain fatty acids such as caprylic acid, capric acid and mixtures thereof. These saturated medium chain fatty acids have the additional benefits of neutral taste, excellent oxidation stability, and low viscosity which yields a readily spreadable product. The triglyceride vegetable oil may comprise from about 30 wt % to about 60 wt % of the dental cream formulation and preferably will make up from about 35% to about 45% of the adhesive cream.

Fumed silica is also used to replace the hydrocarbon petrolatum as the thickener for the adhesive and is added to the vegetable oil for this purpose. A fine white powder, fumed silica is the colloidal form of silica (silicon dioxide, $SIO_2$) made by the combustion of silica tetra-chloride in a hydrogen-oxygen furnace. The amount of fumed silica used in the composition may range from about 1.0% to about 6.0%. The amount is important since it was found that above 6.0% the viscosity increases, the cream becomes much more difficult to extrude from the tube and the stability of the cream at elevated temperatures is a problem.

The basic polymer of the denture adhesive base composition that gives the cream its body, texture and adhesive qualities is a lower alkyl vinyl ether/malic anhydride copolymer and the mixed partial salts thereof such as the calcium/sodium partial salt. These copolymers are well known in the art and their preparation is disclosed in U.S. Pat. No. 4,569,955 to Dhabhar and the U.S. Pat. No. 3,003,988 to Germann et. al. which are hereby incorporated by reference. The preferred poly(methyl vinyl ether/maleie anhydride) copolymer is Gantrez AN (ISP, U.S.A.). The methyl vinyl ether/maleie anhydride copolymer salt will generally comprise from about 20% to about 40% of the dental cream formulation and preferably from about 25% to about 35% of the formulation.

The dental adhesive formulations of the present invention further comprise a water soluble cellosic polymer as is known in the art such as methyl cellulose, carboxymethyl cellulose, sodium carboxymethyl cellulose, hydroxypropyl methyl cellulose and the like. The cellosic polymer, preferably carboxymethyl cellulose, is a powder which, when moistened, becomes hydrated and tacky or gummy in consistency thereby providing additional adhesive functionality to the dental cream composition. These carboxymethyl cellulose gums are water soluble, anionic long chain polymers whose properties vary to some extent depending on the number of carboxymethyl groups that are substituted per anhydroglucose unit in each cellulose molecule. These cellulose polymers comprise from about 20% to about 35%, and preferably form about 22% to about 28% of the dental adhesive formulation.

Other minor components make up the remaining elements of the composition and include dyes for coloring, flavors for improved taste and preservatives for long term stability. The types and amounts are well known in the art and generally vary between 0.05% to about 1.0% depending on ones own preference. These can be formulated as a spreadable viscous paste or gel or as a hydratable powder which can be sprinkled about the dentures and is swellable once it is placed in the mouth.

The following examples are provided to more fully disclose and describe the formulations that comprise the present invention and the manner of making them. They are for illustrative purposes only however and it is recognized that numerous minor changes or variations can be made to the ingredients or the parameters of the process for making the formulations that are not disclosed herein. It is to be understood that any such changes which do not materially affect or alter the final product or the manner in which it is produced are still considered as falling within the spirit and scope of the invention as recited by the claims that follow.

Example I

The following components were collected in their respective weight percents.

|  | Percent |
| --- | --- |
| Caprylic/Capric triglyceride blend | 41.39 |
| Fumed silica | 4.10 |
| Carboxymethyl cellulose | 24.0 |
| Gantrez salt (methyl vinyl ether/malic anhydride polymer calcium salt) | 30.00 |
| Dyes | 0.06 |
| Flavors | 0.4 |
| Preservatives | 0.05 |

The caprylic/capric triglyceride is first mixed with the fumed silica until a clear to translucent uniform base vehicle is formed. FD&C dyes may be added at this time or may be left out if a color may be selected according to taste.

The carboxymethyl cellulose was slowly added and mixed into the base until all of it is uniformly dispersed. The Gantrez® salt was similarly added and dispersed in the same manner. All ingredients were continually mixed at low speed for thirty (30) minutes with care being taken to scrape the sides of the mixing bowl to insure uniform dispersal. Flavors such as spray dried peppermint or spray dried spearmint were added for taste along with the preservatives as is know is the art to prevent spoilage during long term shelf storage.

It was determined that thickening caprylic/capric triglycerides with 3.6–4.1 wt % fumed silica yielded a soft, pliable denture adhesive with excellent tack and exceptional adhesion and cohesion strength.

Example II

Two denture adhesive formulations were prepared according to Example I with 3.6 wt % and 4.0 wt % fumed silica, respectively, all other ingredients remaining constant. The shear strength of these two adhesives was then compared to a mineral oil/petrolatum base formula as is known in the art. The shear strength of an adhesive is indicative of its ability to securely and stably affix the dental plate to the gums and withstand the mandibular pressures exerted thereon. The comparative shear strengths of these adhesives was determined using the normal coth method procedure on an Instron Model #Instron/Canton, Mass. which allowed the samples to hydrate with water prior to taking the shear strength measurements. The results are as follows:

TABLE 1

| Denture Adhesives | Shear Results ($g/inch^2$ vs. time) | | | | | |
| --- | --- | --- | --- | --- | --- | --- |
| Caprylic/capric triglycerides with 3.60% fumed silica base | 249.7 10 min | 295.1 40 min | 227.0 70 min | 113.5 100 min | 113.5 130 min | 96.0 160 min |
| Caprylic/capric triglycerides with 4.10% fumed silica base | 272.0 10 min | 499.4 40 min | 272.4 70 min | 172.8 100 min | 136.0 130 min | 96.8 160 min |
| Mineral oil/ petrolatum base | 181.6 10 min | 204.3 40 min | 136.2 70 min | 113.5 100 min | 68.1 130 min | 45.1 160 min |

The results clearly indicate that the new vehicle adhesives, as embodied by the two samples above have higher shear values and maintain their hold strength for a longer period of time than the mineral oil/petrolatum vehicle adhesives known in the art.

The performance characteristics of the new denture adhesive with the hydrocarbon-free base was also evaluated and compared to the mineral oil/petrolatum base formula known in the art in an in-house consumer test. Whereas these results were at parity, the new denture adhesive product was preferred for ease of application, ease of removal and ease of extrudability. The odor of the product was found to be pleasing both at room and elevated temperatures. This would clearly indicate that caprylic/capric triglycerides are a more suitable, hydrocarbon-free vegetable off with excellent oxidation stability and is the appropriate carrier for fumed silica. The combination of the two is a tacky transparent vehicle that is very consistent with mineral oil/petrolatum base and the adhesive prepared with this base does not become rancid under the effect of heat or oxygen. Also, the adhesive maintains its original stability and no viscosity increase and/or extrudability problems are seen.

Example III

The denture adhesives prepared according to the formulations set forth in Example I were also compared with similar compositions in which the base, comprised of capric/caprylic acid triglycerides with fumed silica, was replaced with bases comprised of hybrid safflower oil thickened with polyethylene and fumed silica, soybean oil thickened with microcrystalline wax and fumed silica, castor oil, peanut oil and avocado oil. All other components of the adhesive and their respective amounts remained constant. The adhesive and cohesive strength of the compositions comprised of eaprylic/capric triglycerides thickened with fumed silica were superior to all other formulas prepared with the other above mentioned vegetable oils thickened with waxes, polyethylene and fumed silica. Their odor and taste, their ability to absorb water, quick hydrating rate, their rapid spreadability and their non-greasy afterfeel characteristics were excellent. After three months, the stability among all formulas prepared was compared and the most stable formula, with pleasing odor, taste and hold properties were the formulas prepared with caprylic/capric triglycerides thickened with 2.0 to 6/0% fumed silica. The other vegetable oils produced adhesive creams that were unstable at elevated temperatures with regard to taste, odor or oxidative stability thereby yielding a bitter, sometimes rancid taste and off-color in the final product.

What we claim is:

1. An improved, hydrocarbon-free denture adhesive comprising:
   a. a saturated medium chain fatty acid triglyceride base thickened with fumed silica;
   b. a water soluble polymer selected from the group comprising cellulose derivatives;
   c. a methyl vinyl ether/maleic anhydride polymer, it's salts; and
   d. flavors, preservatives and other excipients.

2. The denture adhesive of claim 1 wherein said fatty acid triglyceride is selected from the group consisting of caprylic triglycerides, capric triglycerides and mixtures thereof.

3. The denture adhesive of claim 2 wherein said vegetable oil comprises from about 30 wt % to about 60 wt % of the total weight of the adhesive composition.

4. The denture adhesive of claim 3 wherein said vegetable oil comprises from about 35 wt % to about 45 wt % of the total weight of the composition.

5. The denture adhesive of claim 4 wherein said fumed silica is present in an amount of from about 2.0 wt % to about 6.0 wt % of said denture adhesive.

6. The denture adhesive of claim 5 wherein said fumed silica comprises from about 3.5 wt % to about 4.5 wt % of the total weight of the denture adhesive composition.

7. The denture adhesive of claim 6 wherein said water soluble cellulose-derived polymer is selected from the group consisting of methyl cellulose, carboxymethyl cellulose, sodium carboxymethyl cellulose, hydroxypropyl methyl cellulose, and mixtures thereof.

8. The denture adhesive of claim 7 wherein said water soluble cellulose-derived polymer comprises from approximately 20 wt. % to about 35 wt. % of the total weight of the dental composition.

9. The denture adhesive of claim 8 formulated as a viscous paste or gel.

10. An improved hydrocarbon-free denture adhesive comprising a base consisting essentially of saturated medium chain fatty acid triglycerides with a fumed silica thickener, a water-soluble cellulose-derived polymer and a synthetic copolymer, said adhesive exhibiting excellent adhesive and cohesive properties and is readily spreadable about the oral mucosa.

11. The improved denture adhesive of claim 10 wherein said fatty acid triglyceride is selected form the group consisting of capric acid, caprylic acid and mixtures thereof.

12. The denture adhesive of claim 11 wherein said fatty acid triglycerides comprise from about 30 wt. % to about 60 wt. % of the total weight of the adhesive composition.

13. The denture adhesive of claim 12 wherein said fatty acid triglyceride comprises from about 35 wt. % to about 45 wt. % of the total weight of the composition.

14. The denture adhesive of claim 13 wherein said fumed silica is present in an amount of from about 2.0 wt % to about 6.0 wt % of the denture adhesive composition.

15. The denture adhesive of claim 14 wherein said fumed silica comprises from about 3.5 wt. % to about 4.5 wt. % of the denture adhesive composition.

16. The denture adhesive of claim 15 wherein said cellulose-derived polymer is selected from the group consisting of methyl cellulose, carboxymethyl cellulose, sodium carboxymethyl cellulose, hydroxypropyl methyl cellulose and mixtures thereof.

17. The denture adhesive of claim 16 wherein said synthetic copolymer is selected from the group comprising methyl vinyl ether maleic anhydride copolymer, its salts and mixtures thereof.

18. The denture adhesive of claim 17 wherein said water soluble cellulose derived polymer comprises from approximately 20 wt. % to about 35 wt. % of the total weight of the dental composition.

19. The denture adhesive of claim 18 wherein said water soluble cellulosic polymer is selected from the group consisting of carboxymethyl cellulose, sodium carboxymethyl cellulose and mixtures thereof.

20. The denture adhesive of claim 18 wherein said water soluble cellulose-derived polymer is selected from the group consisting of carboxymethyl cellulose, sodium carboxymethyl cellulose and mixtures thereof.

\* \* \* \* \*